US008815862B2

(12) United States Patent
Ferrari et al.

(10) Patent No.: US 8,815,862 B2
(45) Date of Patent: Aug. 26, 2014

(54) CO-CRYSTAL INTERMEDIATES OF ROSUVASTATIN AND METHODS OF USING SAME

(71) Applicant: F.I.S. Fabbrica Italiana Sintetici S.p.A., Alte di Montecchio Maggiore (IT)

(72) Inventors: Clark Ferrari, Vicenza (IT); Andrea Castellin, Padua (IT); Marco Galvagni, Verona (IT); Nicolas Tesson, Barcellona (ES); Jordi De Mier, Barcellona (ES); Llorenç Rafecas, Barcellona (ES)

(73) Assignee: F.I.S. Fabbrica Italiana Sintetici S.p.A., Montecchio Maggiore (VI) (IT)

( * ) Notice: Subject to any disclaimer, the term of this patent is extended or adjusted under 35 U.S.C. 154(b) by 0 days.

(21) Appl. No.: 13/691,881

(22) Filed: Dec. 3, 2012

(65) Prior Publication Data
US 2013/0143890 A1 Jun. 6, 2013

(30) Foreign Application Priority Data

Dec. 6, 2011 (EP) .................................... 11192188

(51) Int. Cl.
*C07D 241/42* (2006.01)
*C07D 239/69* (2006.01)
*C07D 241/12* (2006.01)
*C07D 239/42* (2006.01)

(52) U.S. Cl.
CPC ............ *C07D 241/42* (2013.01); *C07D 239/42* (2013.01); *C07D 239/69* (2013.01); *C07D 241/12* (2013.01)
USPC ...... 514/249; 514/255.05; 514/275; 544/297; 544/296; 544/295

(58) Field of Classification Search
CPC ....................................................... C07D 239/42
USPC ............. 514/249, 255.05, 275; 544/295, 296, 544/297
See application file for complete search history.

(56) References Cited

U.S. PATENT DOCUMENTS

| 6,841,554 B2 * | 1/2005 | Taylor et al. ................... 514/275 |
| 2007/0225299 A1 * | 9/2007 | Bischoff et al. ............... 514/256 |
| 2011/0275649 A1 * | 11/2011 | Kaesemeyer ............ 514/254.03 |

FOREIGN PATENT DOCUMENTS

| EP | 0521471 A1 | 1/1993 |
| WO | WO 2007079916 A2 * | 7/2007 |
| WO | WO 2007125547 A2 * | 11/2007 |
| WO | 2008119810 A2 | 10/2008 |
| WO | WO 2008157537 A2 * | 12/2008 |
| WO | 2009118598 A1 | 10/2009 |
| WO | 2009128091 A2 | 10/2009 |
| WO | WO 2010081861 A1 * | 7/2010 |
| WO | 2012069394 A1 | 5/2012 |

* cited by examiner

*Primary Examiner* — Samantha Shterengarts
*Assistant Examiner* — Amanda L Aguirre
(74) *Attorney, Agent, or Firm* — Robert E. Alderson, Jr.

(57) ABSTRACT

Methods for the preparation of Rosuvastatin by co-crystals of Rosuvastatin or intermediates are provided. Also provided are co-crystals, pharmaceutical compositions which include such co-crystals and methods for treating conditions associated with hypercholesterolemia by administering such compositions.

12 Claims, 9 Drawing Sheets

CO-CRYSTAL INTERMEDIATES OF ROSUVASTATIN AND METHODS OF USING SAME

CROSS REFERENCE TO RELATED APPLICATION

This application claims priority to and benefit of European Patent Application No. 11192188.8 filed Dec. 6, 2011, the contents of which are incorporated by reference in their entirety.

FIELD OF THE INVENTION

The present invention relates to methods for the preparation of the active pharmaceutical ingredient Rosuvastatin.

BACKGROUND OF THE INVENTION

Rosuvastatin is an active pharmaceutical ingredient (API) having the chemical name (E)-(3R,5S)-7-[4-(4-Fluorophenyl)-6-isopropyl-2-[(methylsulfonyl)(methyl)amino]pyrimidin-5-yl]-3,5-dihydroxyhept-6-enoic acid and having structural formula (I):

Rosuvastatin and other APIs belonging to the same family of statins, are characterized by the presence of two oxydrilic groups bound to asymmetric carbon atoms which are part of a side chain linked to a pyrimidine ring. Rosuvastatin is currently marketed as a calcium salt (Rosuvastatin calcium), or as a hemicalcium salt of formula (II):

having the chemical name 6-Heptenoic acid, 7-[4-(4-fluorophenyl)-6-(1-methylethyl)-2-[methyl (methylsulfonyl)amino]-5-pyrimidinyl]-3,5-dihydroxy-, calcium salt (2:1), (3R,5S,6E)- and with commercial names such as Crestor®, Fortius®, Rostar® and Rozavel®.

Rosuvastatin is an inhibitor of 3-Hydroxy-3-Methylglutaryl-Coenzime A (HMG-CoA) reductase, the enzyme that catalyzes the conversion of HMG-CoA to Mevalonate, a limiting agent of the biosynthesis of Cholesterol and it is therefore used to treat and prevent hypercholesterolemia, to promote the regression of atherosclerotic plaque and to prevent cardiovascular events.

Several methods for the synthesis of this API are disclosed in the literature. Such methods are described, for example, in EP0521471A1, in particular in Example 1, and more recently in WO2009/128091 and WO2009/118598. Several such methods are directed to improving the quality of the product by means of the purification of a relatively early intermediate in the form of Rosuvastatin methyl or ethyl ester. However, this intermediate, to be converted to Rosuvastatin, must be hydrolized and thus during this step Rosuvstatin may racemize, thereby decreasing the optical purity of the final compound.

SUMMARY OF THE INVENTION

The problem addressed by the present invention is therefore that of providing alternative methods for the preparation of Rosuvastatin and salts thereof which overcome the problems reported in the prior art.

These problems are solved by methods for the preparation of Rosuvastatin which utilize novel co-crystal intermediates as described herein.

DETAILED DESCRIPTION

The present invention provides methods for the preparation of Rosuvastatin and/or its salts comprising the steps of:
(a) preparing a co-crystal of Rosuvastatin selected from the group consisting of:

1. Rosuvastatin 2-aminopyrimidine hemihydrate,
2. Rosuvastatin pyrazine hydrate, and
3. Rosuvastatin quinoxaline (1:2);

(b) converting of the co-crystal prepared in step (a) to Rosuvastatin of formula (I) and/or its salts.

In certain embodiments, methods according to the present invention are directed to the preparation of Rosuvastatin calcium salt of formula (II).

It has been surprisingly discovered that it is possible to prepare co-crystals of Rosuvastatin that are useful intermediates for the preparation of Rosuvastatin itself and for of Rosuvastatin salts, such as Rosuvastatin calcium. The newly discovered co-crystals of Rosuvastatin include the following:

a. Rosuvastatin 2-aminopyrimidine hemihydrate,
b. Rosuvastatin pyrazine hydrate,
c. Rosuvastatin quinoxaline (1:2).

These co-crystals exhibit highly unexpected and exceptional properties. This is in sharp contrast to the formation of different crystalline forms of a substance for which it is possible at least to predict the existence by means of proper software. This is confirmed by the fact that co-crystals of only 30% of the APIs containing carboxylic groups marketed in the United States are known.

The three co-crystals of Rosuvastatin described above, according to our knowledge, have never been disclosed in the prior art. Indeed, it is believed that there are no co-crystals of Rosuvastatin disclosed in literature. Thus, the preparation of Rosuvastatin co-crystals is an exceptional and unexpected event, especially considering that Rosuvastatin itself has been known for many years and many studies relating to its preparation have been carried out resulting in large volumes of related literature.

The co-crystal of Rosuvastatin and aminopyrimidine is a hemihydrate form and has molecular formula (III):

(III)

Such co-crystal of Rosuvastatin, also named Rosuvastatin 2-aminopyrimidine hemihydrate, has the formula $C_{22}H_{28}FN_3O_6S \cdot C_4H_5N_3 \cdot 0.5\ H_2O$ and a molecular weight of 585.65 atomic mass units. The molar ratio of the components of this co-crystal is Rosuvastatin:2-aminopyrimidine:water (1:1:0.5).

The co-crystal of Rosuvastatin and pyrazine is a monohydrate form and has molecular formula (IV):

(IV)

This co-crystal is also named Rosuvastatin pyrazine hydrate, has a formula $C_{22}H_{28}FN_3O_6S \cdot C_4H_4N_2 \cdot H_2O$ and a molecular weight of 579.63 atomic mass units. In the co-crystal of rosuvastatin pyrazine hydrate the molar ratio of the component is 1:1:1.

The co-crystal of Rosuvastatin and quinoxaline (1:2) is an anhydrous form and has the molecular formula (V):

(V)

Such co-crystal is also named Rosuvastatin quinoxaline (1:2) and presents two molecules of coformer quinoxaline for each molecule of Rosuvastatin. It has formula $C_{22}H_{28}FN_3O_6S \cdot 2\ C_8H_6N_2$ and a molecular weight of 611.68 atomic mass units. The molar ratio between Rosuvastatin and the coformer is 1:2.

In certain embodiments of the invention, the co-crystal Rosuvastatin 2-aminopyrimidine hemihydrate provides the best results in terms of purity and isolated molar yield, in comparison to the other two co-crystals. The co-crystal of Rosuvastatin 2-aminopyrimidine hemihydrate has a crystal structure characterized by an X-Ray Powder Diffractogram (XRPD) with characteristic peaks expressed in 2 Theta value of: 9.40 (vs), 13.50 (s), 14.08 (m), 15.15 (m), 18.59 (m), 21.67 (m), 22.16 (m), 22.21 (m), 22.66 (m), (+/−) 0.10; wherein (vs)=very strong intensity, (s)=strong intensity, (m)=medium intensity. Furthermore, this co-crystal has a melting point of about 109.4° C.

The preparation of co-crystals of Rosuvastatin according the present invention may be carried out starting from Rosuvastatin in the free acid form or from a salt, preferably an alkaline or an alkaline-earth salt of Rosuvastatin.

The formation of such co-crystals may be carried out from a solution of toluene, MIK or aqueous solution comprising Rosuvastatin and adding a coformer. If necessary, depending on the type of co-crystal prepared, it is optionally possible to add small quantities of water to the organic solvent.

The formation of a co-crystal, according to step (a) may be performed at a temperature below about 40° C., and in certain embodiments between about 30 and about 35° C. In this way it is possible to minimize the formation of the by-product Rosuvastatin lactone, a well-known impurity of Rosuvastatin comprising the inner cyclic ester of Rosuvastatin.

Methods for preparing co-crystals according to the present invention do not require seeding. If seeding is used the precipitation of the co-crystal is typically faster than if it is not used. If seeding is not used, in order to help the formation of the co-crystal it is useful to cool the solution slowly until reaching about 10° C.

It should be noted that solid forms of the present invention are co-crystals and not simply salts. In the literature there are dozens of Rosuvastatin salts described, many of them with amines as contra-ion, but none describe a co-crystal of Rosuvastatin.

Figure 5:
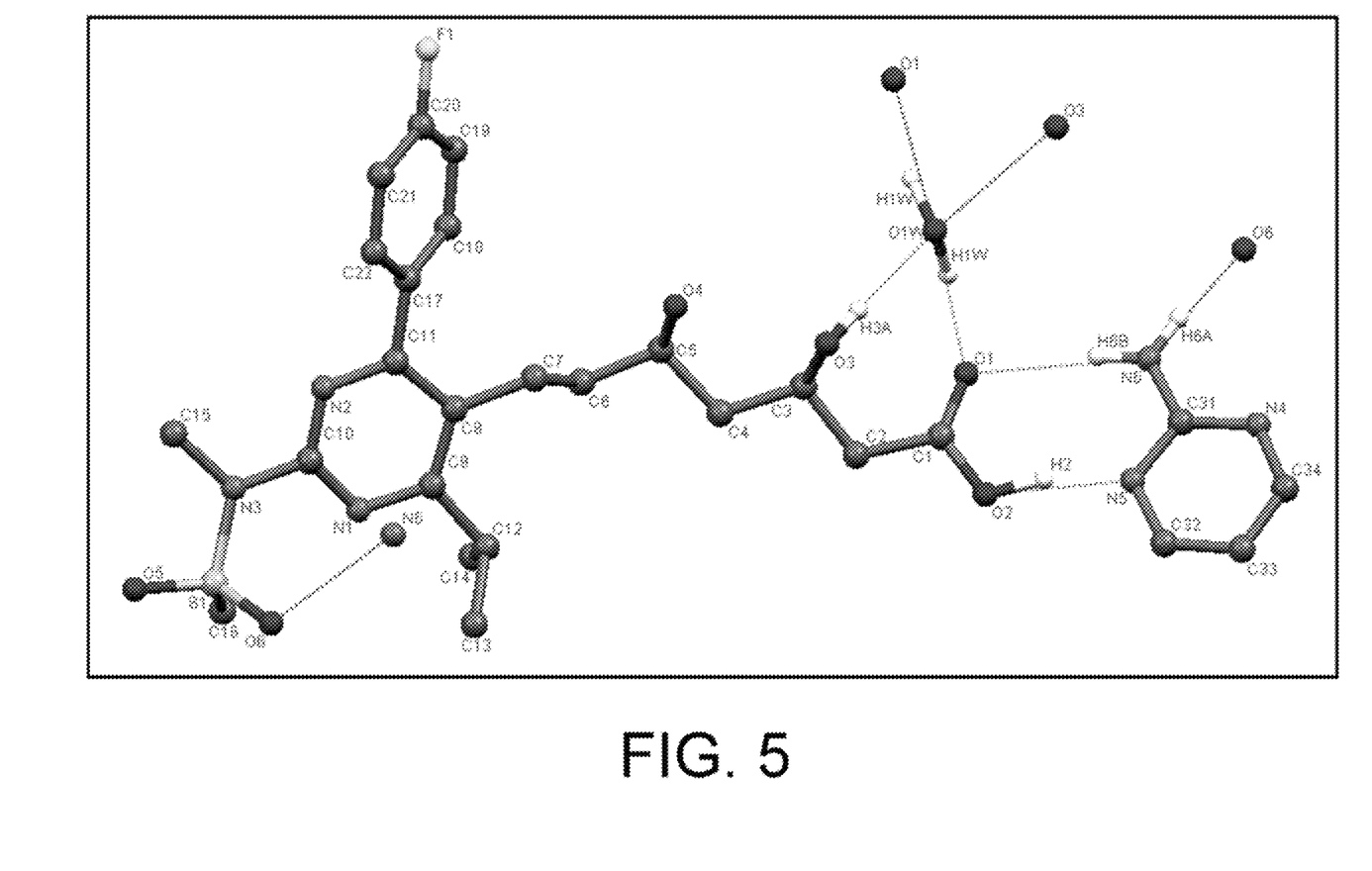
FIG. 5 shows a single crystal structure of the co-crystal Rosuvastatin 2-aminopyrimidine hemihydrate of formula (III).

The preparation of co-crystals is confirmed by the single crystal structure analysis, as discussed infra in Example 9 and as shown in FIG. 5 (co-crystal Rosuvastatin 2-aminopyrimidine hemihydrates of formula (III)) which shows that the carboxylic proton is still part of the Rosuvastatin molecule and it is not bonded on the pyrimidine, as it would be if it were a simple salt. Pyrimidine is therefore a coformer of a co-crystal and not a contra-ion of a salt.

For the other co-crystal forms, Rosuvastatin pyrazine hydrate and Rosuvastatin quinoxaline (1:2), the formation of co-crystals is also confirmed on the basis of the low basicity of these amines (pKa 0.5-0.6): the ΔpKa between Rosuvastatin and these amines is lower than zero confirming the formation of a co-crystal. (See scientific explanation in Example 10).

The above-described co-crystals of Rosuvastatin above may be used as synthetic intermediates for the preparation of Rosuvastatin and/or salts thereof.

In particular, methods of the present invention allow the preparation of Rosuvastatin with a surprisingly high degree of chemical purity and optical purity in comparison with Rosuvastatin prepared using Rosuvastatin salts, such as the Rosuvastatin cyclohexylamine salt. See, for example, the comparative table below where the co-crystal and the salt are prepared from the same batch of Rosuvastatin sodium salt (RSVNa).

TABLE 1

| | Chemical Purity (HPLC A %) |
|---|---|
| RSVNa starting material | 98.70 |
| RSV Cyclohexylamine salt | 99.20 |
| Co-cristal RSV 2-aminopyrimidine | 99.96 |

An important advantage of methods according to the present invention is that further steps for purification of the co-crystal in order to reach the purity level necessary for the preparation of Rosuvastatin of pharmaceutical grade are not required. This is in contrast to what is typically required when preparing Rosuvastatin by means of salts thereof.

The crystallization in MIK (Methylisobutylketone) of the co-crystal Rosuvastatin 2-aminopyrimidine hemihydrate from RSVNa (without the isolation of the acid Rosuvastatin) provides excellent purity (99.96%, without taking account of 2-aminopyrimidine) with a good yield (typically at least 70%).

The profile of Rosuvastatin is summarized below:
Purity >99.9% HPLC (without taking account of 2-aminopyrimidine).
No impurity >0.1%.

The typical molar yield of step (a), determined by a mass balance study, is between 76% and 86%. Highest values were reached by isolating the product from 4 volumes of solvent MIK and washing the product with 2×1 volume of MIK pre-cooled at −10° C. Nevertheless, best values of purity, while keeping relatively high values of molar yield, are reached by washing the product with 2×0.5 volumes of MIK pre-cooled at about 0° C.

Methods for preparing Rosuvastatin, according to step (b), provides Rosuvastatin or Rosuvastatin salt, such as Rosuvastatin calcium, from the co-crystal of Rosuvastatin prepared in the step (a).

The co-crystal Rosuvastatin may be disaggregated by an aqueous solution of a base, e.g. NaOH. Then, the aqueous phase may be washed with an organic solvent. After striping, the combined aqueous phases may be added to a solution of Calcium chloride. After the precipitation of RSVCa, the residual included 2-aminopyrimidine was removed with a water slurrying at 50° C. to result in RSV free from the coformer impurity.

The RSVCa prepared in step (b) has an impurities profile identical to the co-crystal prepared in step (a) (similar amounts of the same impurities) with an overall yield of 65% (2 steps). The small scale of these experiments and the significant volume of water could explain this moderate yield. Scale-up and optimization will improve the isolated final molar yield. In the optimized process, precipitation of RSVCa with complete elimination of the coformer, can be carried out in a one-pot process.

From RSVNa aqueous solution, RSVCa was obtained with an excellent purity of 99.93%.

Other advantages of methods according to the present invention based on the preparation of the synthetic intermediate co-crystals, such as the co-crystal Rosuvastatin 2-aminopyrimidine hemihydrates, include:
  the ability to crystallize the co-crystal without isolating the Rosuvastatin in acid form thereby avoiding the formation of the lactone by-product.
  industrial applicability: solvent class III (MIK) and high concentration (4-10 vol.), preferable lower than 5 volumes.
  the filtration of the co-crystal is easy and the solid has good handling properties.
  stability:
  Co-crystals of the present invention have a relative lack of polymorphism due to the higher complexity of the crystal structure: polymorphs of co-crystal Rosuvastatin 2-aminopyrimidine hemihydrate were not observed during screening and studies of the purification of Rosuvastatin. In contrast, form salts of Rosuvastatin amines having different polymorphs.

Co-crystal Rosuvastatin 2-aminopyrimidine hemihydrate stored at room temperature in a sealed vial for 3 weeks does not show crystalline transformation (same XRPD) or loss of crystallinity.

Humidity: co-crystal stored at room temperature with a RH of 100% for 24 h shows the same XRPD without loss of crystallinity. Moreover, the solid maintains its good handling properties.

Co-crystal Rosuvastatin 2-aminopyrimidine hemihydrate has a chemical stability higher than the Rosuvastatin acid (especially avoiding the formation of the lactone by-product) as confirmed by the stability study described in Example 11.

The 2-aminopyrimidine co-former has low toxicity. Moreover, it is highly soluble in water and is thus easy to remove during the subsequent formation of the Rosuvastatin Calcium (RSVCa) salt of formula (II).

The purification obtained is excellent (from HPLC purity of 98.7% of Rosuvastatin Sodium (RSVNa) as starting material to higher than 99.9% of Rosuvastatin co-crystal intermediate) with only one crystallization and the yield is good (typically >70%).

The solubility of co-crystal Rosuvastatin 2-aminopyrimidine hemihydrate in a series of solvents at room temperature is provided in Table 2 given below:

TABLE 2

| ACN: | 14 vol. |
|---|---|
| MeOH: | 3 vol. |
| EtOH: | 10 vol. |
| AcOEt: | 20 vol. |
| Acetone: | 4 vol. |
| MIK: | 45 vol. |
| THF: | 2 vol. |

The co-crystals of Rosuvastatin described herein are useful for use in medicine.

In particular these co-crystals can be used to address all forms of hypercholesterolemia. Especially useful for this purpose is the co-crystal comprising pyrazine of formula (IV).

Co-crystals of the present invention therefore can be formulated in proper pharmaceutical compositions comprising a co-crystal of Rosuvastatin and one or more pharmaceutically acceptable excipients, carriers or diluents. An example of possible excipients useful for the pharmaceutical composition comprising a co-crystal of the present invention: microcrystalline cellulose, lactose monohydrate, tribasic calcium phosphate, crospovidone, magnesium stearate, hypromellose, triacetin, titanium dioxide, yellow ferric oxide, and red ferric oxide.

EXAMPLES

Example 1

Preparation and Characterization of the Co-crystal Rosuvastatin 2-minopyrimidine Hemihydrate of Formula (III)

(III)

Preparation

Note: RSVNa may be prepared according EP0521471A1 and RSV may be prepared from RSVNa with acidic treatment and extraction with organic solvent. (See example 4)

To an assay tube equipped with magnetic stirrer containing Rosuvastatin (as acid form) (RSV) (62 mg, 0.13 mmol) and 2-aminopyrimidine (13 mg, 0.13 mmol) was added toluene (0.75 mL, 10 vol.) before heating to 110° C. The resulting solution was allowed to cool to room temperature (24-28° C.) resulting in the precipitation of a white solid. The crude was filtered through a sintered glass funnel (n° 4) to provide 38 mg of the co-crystal Rosuvastatin 2-aminopyrimidine hemihydrate with a molar yield of 49%.

1H-NMR Characterization

Proton nuclear magnetic resonance analyses were recorded in deuterated dimethyl sulfoxide (DMSO-d6) in a Varian Mercury 400 spectrometer, equipped with a broadband probe ATB 1H/19F/X of 5 mm. Spectra were acquired dissolving 5-10 mg of sample in 0.6 mL of deuterated solvent.

1H-NMR (DMSO, 400 MHz): $\delta$=8.20 (d, J=4.7 Hz, 2H); 7.76-7.69 (m, 2H); 7.32-7.24 (m, 2H); 6.58-6.47 (m, 4H); 5.54 (dd, J=5.9 Hz, J=16.0 Hz, 1H); 4.20 (q, J=6.6 Hz, 1H); 3.89-3.78 (m, 1H); 3.55 (s, 3H); 3.49-3.39 (m, 4H); 2.30 (dd, J=4.7 Hz, J=14.5 Hz, 1H); 2.20 (dd, J=8.2 Hz, J=14.5 Hz, 1H); 1.60-1.48 (m, 1H); 1.45-1.35 (m, 1H); 1.22 (d, J=6.6 Hz, 6H).

Figure 1:
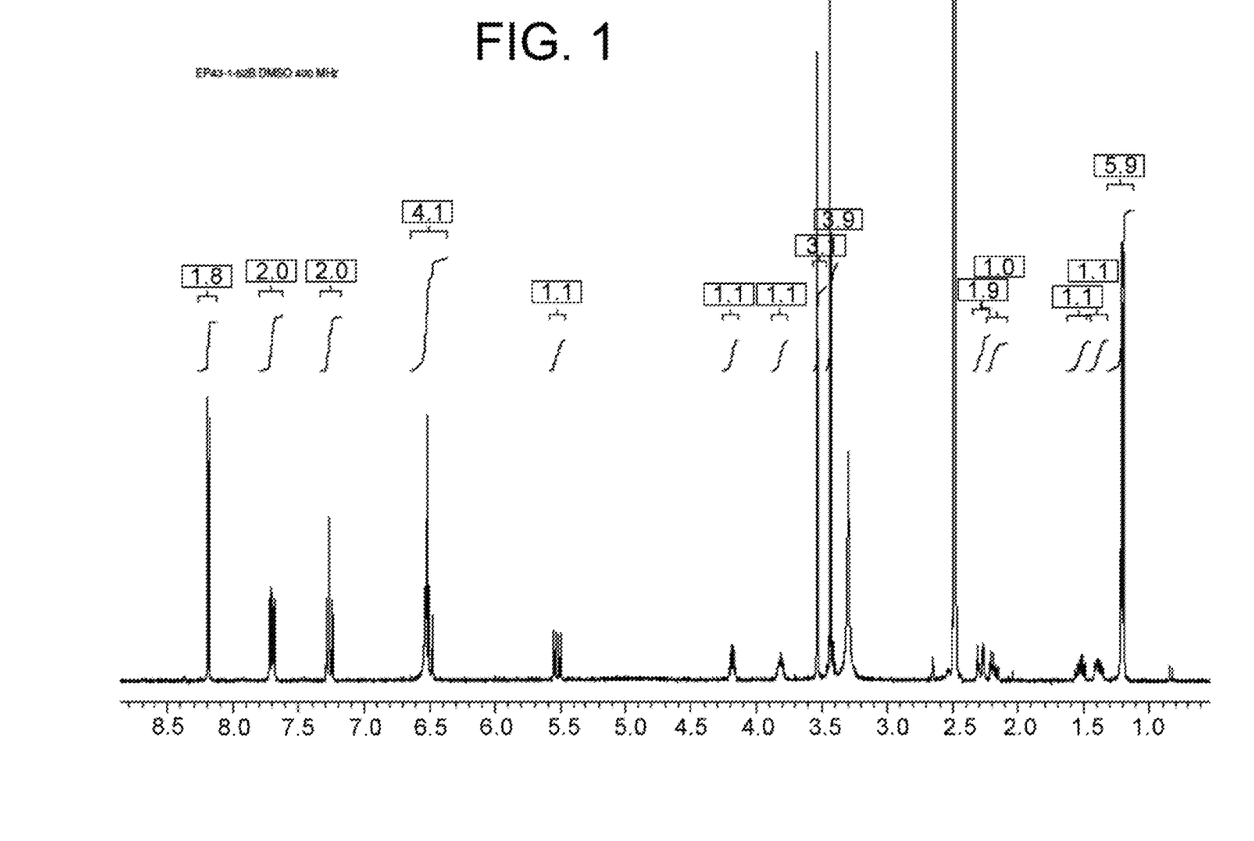
FIG. 1 shows a proton Nuclear Magnetic Resonance (1H-NMR) spectrum of the co-crystal Rosuvastatin 2-aminopyrimidine hemihydrate of formula (III).

(See FIG. 1—1H-NMR)

X-Ray Powder Diffraction (XRPD) Characterization

XRPD analysis was performed using a Philips X'Pert diffractometer with Cu K$\alpha$ radiation in Bragg-Brentano geometry. The system is equipped with a mono-dimensional, real time multiple strip detector. The diffractogram was recorded from 3° to 40° (2$\theta$) at a scan rate of 17.6° per minute (see FIG. 2).

List of selected peaks (only peaks with relative intensity greater than or equal to 1% are indicated):

TABLE 3

| Pos. [°2Th.] | d-spac. [Å] | Rel. Int. [%] |
|---|---|---|
| 9.40 | 9.41 | 100 |
| 10.49 | 8.43 | 2 |
| 11.81 | 7.49 | 6 |
| 12.65 | 7.00 | 7 |
| 13.50 | 6.56 | 55 |
| 14.08 | 6.29 | 29 |
| 15.15 | 5.85 | 24 |
| 16.84 | 5.26 | 7 |
| 17.92 | 4.95 | 7 |
| 18.32 | 4.84 | 16 |
| 18.59 | 4.77 | 29 |
| 18.82 | 4.71 | 9 |
| 19.03 | 4.66 | 8 |
| 19.53 | 4.55 | 3 |
| 20.10 | 4.42 | 11 |
| 20.40 | 4.35 | 15 |
| 20.94 | 4.24 | 2 |
| 21.67 | 4.10 | 33 |
| 22.16 | 4.01 | 34 |
| 22.21 | 4.00 | 36 |
| 22.66 | 3.92 | 32 |
| 23.67 | 3.76 | 14 |

TABLE 3-continued

| Pos. [°2Th.] | d-spac. [Å] | Rel. Int. [%] |
|---|---|---|
| 24.21 | 3.68 | 4 |
| 25.24 | 3.53 | 4 |
| 25.63 | 3.48 | 8 |
| 25.92 | 3.44 | 14 |
| 26.32 | 3.39 | 4 |
| 27.14 | 3.29 | 4 |
| 27.75 | 3.22 | 8 |
| 28.68 | 3.11 | 4 |
| 29.16 | 3.06 | 5 |
| 29.52 | 3.03 | 4 |
| 30.12 | 2.97 | 6 |
| 30.59 | 2.92 | 4 |
| 32.25 | 2.78 | 1 |
| 33.12 | 2.71 | 1 |
| 33.52 | 2.67 | 2 |
| 34.02 | 2.64 | 4 |
| 35.99 | 2.50 | 2 |
| 36.55 | 2.46 | 1 |
| 37.26 | 2.41 | 1 |
| 38.58 | 2.33 | 2 |

Figure 2:
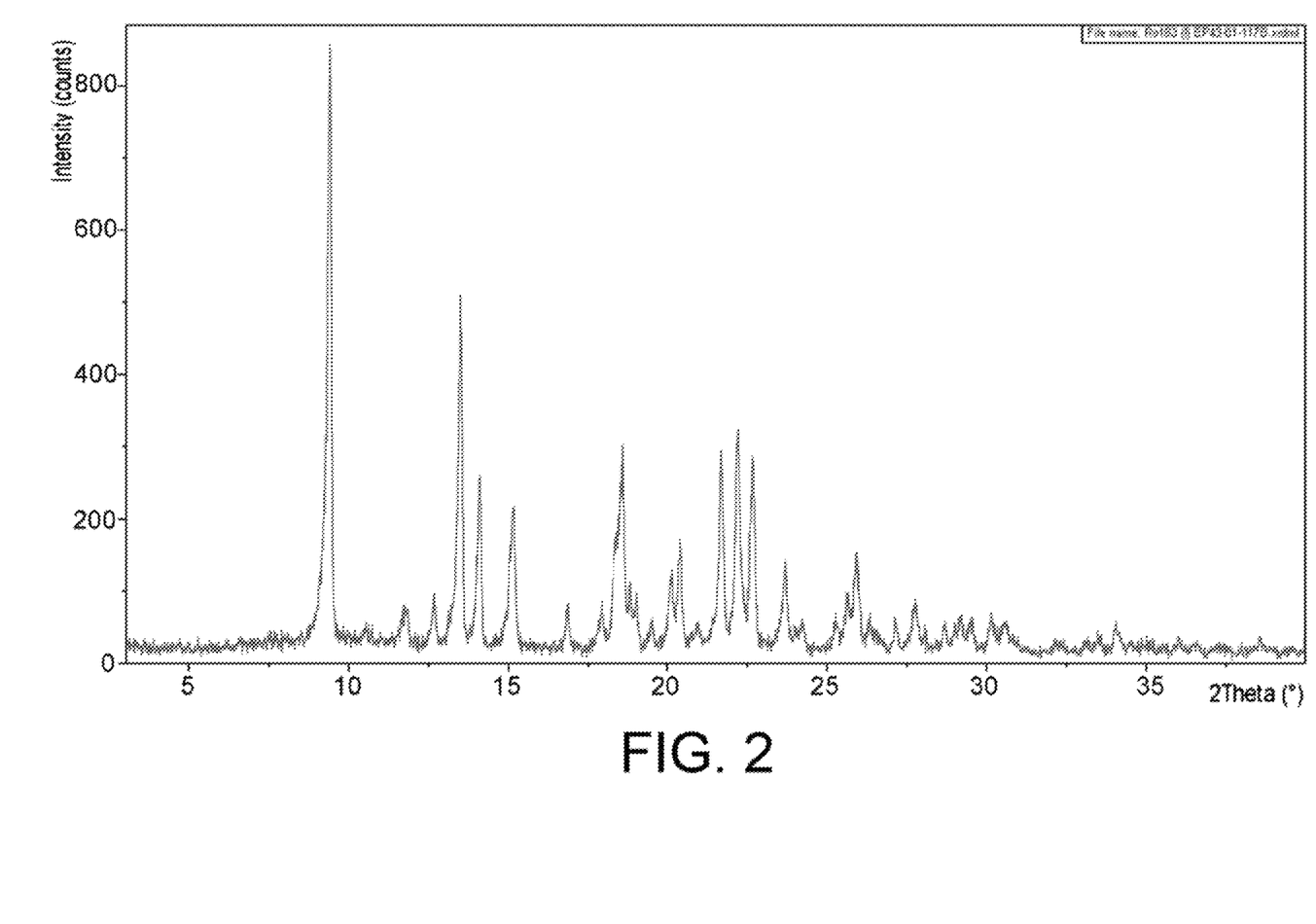
FIG. 2 shows a X-Ray Powder Diffraction (XPRD) diffractogram of the co-crystal Rosuvastatin 2-aminopyrimidine hemihydrate of formula (III).

(See FIG. 2—XRPD Diffractogram).

DSC Characterization

DSC analyses were recorded with a Mettler DSC822e. A sample of 1.7540 mg was weighed into a 40 μL aluminium crucible with a pinhole lid and was heated, under nitrogen (50 mL/min), at 10° C./min from 30 to 300° C.

The co-crystal Rosuvastatin 2-aminopyrimidine hemihydrate shows an endothermic sharp peak corresponding to the melting point with an onset at 109.37° C. (fusion enthalpy −70.77 J/g).

Figure 3:
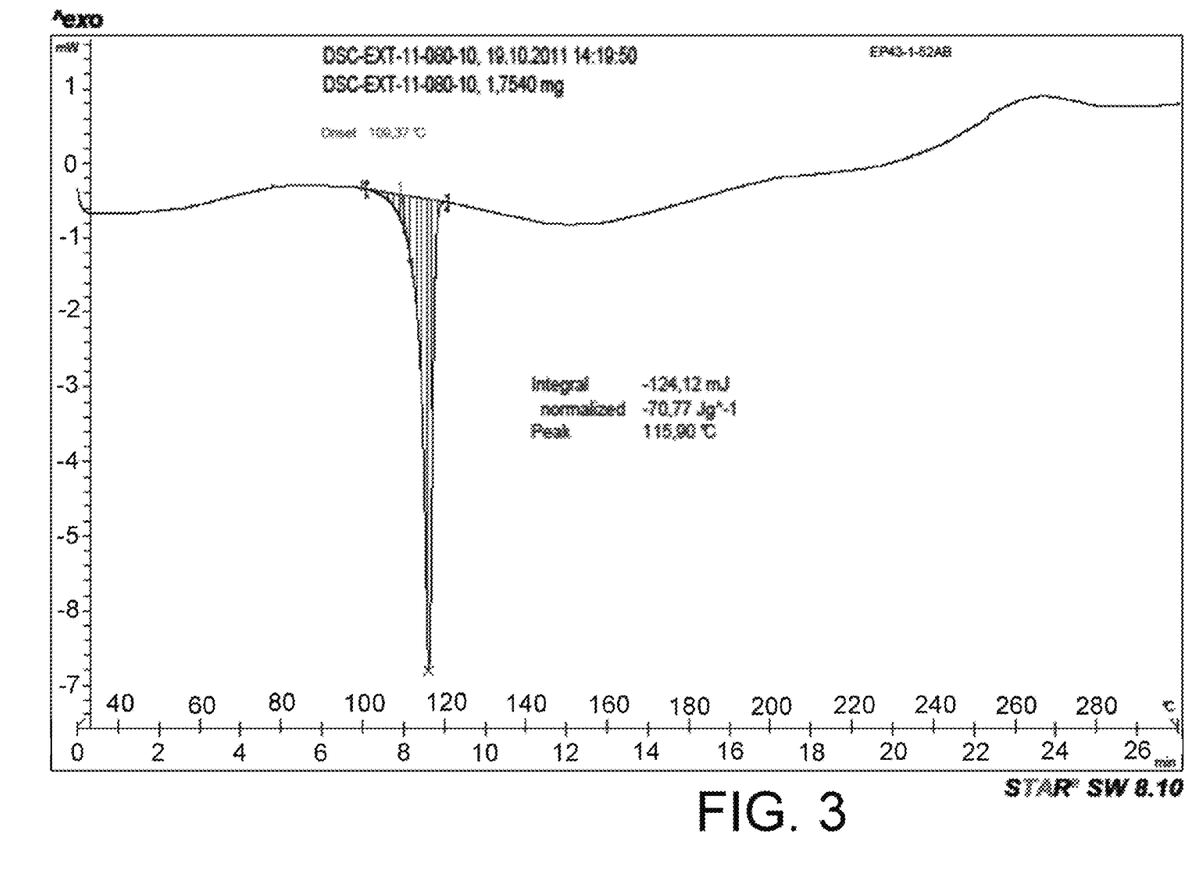
FIG. 3 shows a Differential Scanning calorimetry (DSC) curve of the co-crystal Rosuvastatin 2-aminopyrimidine hemihydrate of formula (III).

(See FIG. 3—DSC).

TGA Characterization

Thermogravimetric analyses were recorded in a thermogravimetric analyzer Mettler TGA/SDTA851e. A sample of 5.2206 mg was weighed into a 70 μL alumina crucible with a pinhole lid and was heated at 10° C./min from 30 to 300° C., under nitrogen (50 mL/min).

The TG analysis of the co-crystal shows 1.26% weight loss before the melting point.

Figure 4:
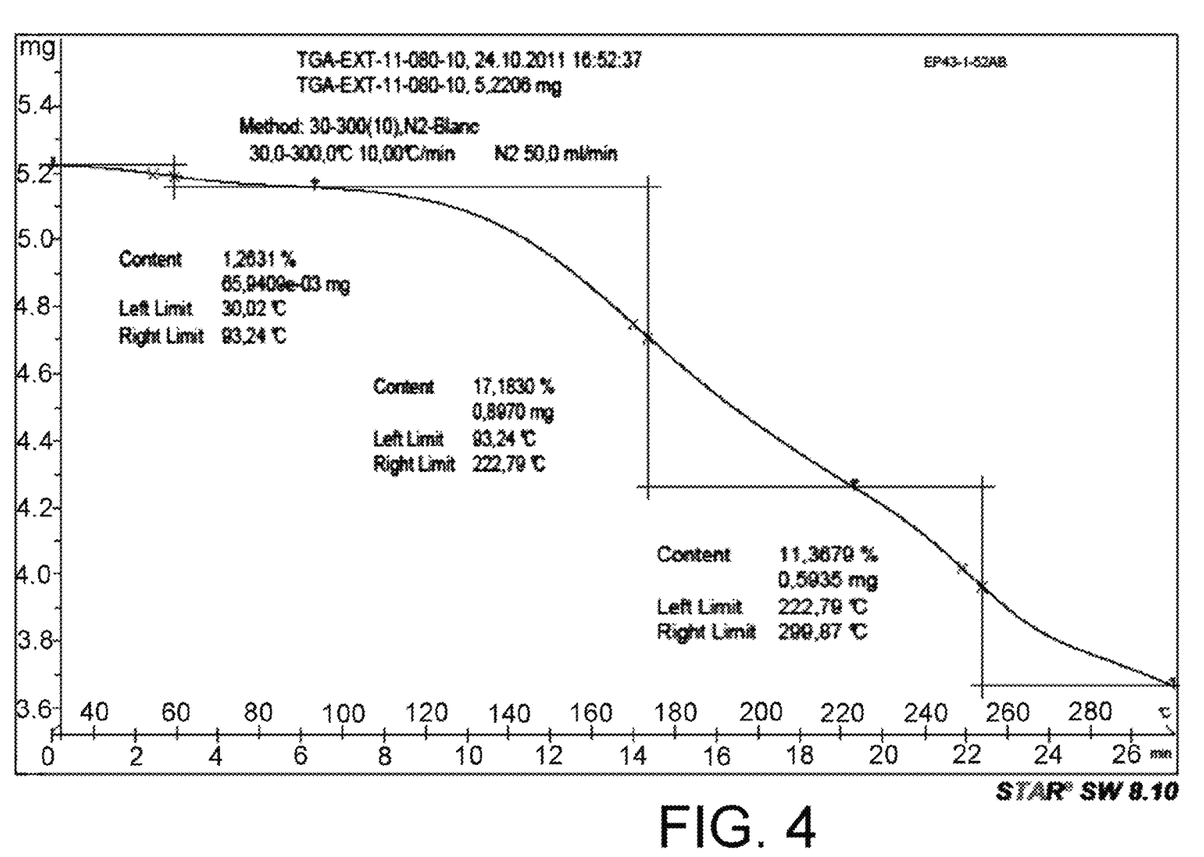
FIG. 4 shows a ThermoGravimetric (TG) curve of the co-crystal Rosuvastatin 2-aminopyrimidine hemihydrate of formula (III).

(See FIG. 4—TGA).

Single Crystal X-ray Diffraction Characterization

The crystal structure of the co-crystal Rosuvastatin 2-aminopyrimidine hemihydrate was determined from single crystal X-ray diffraction data. The colourless prism used (0.36× 0.27×0.07 mm) was obtained from the crystallization from a solution of starting products in toluene. The single crystal structural data are shown in Table 4:

TABLE 4

| Crystal system | Monoclinic |
|---|---|
| Space group | C2 |
| a (Å) | 18.7043(15) |
| b (Å) | 8.2230(7) |
| c (Å) | 18.8025(15) |
| β (°) | 91.182(2) |
| Volume (Å3) | 2891.3(7) |
| Z | 4 |
| D calc. (Mg/m3) | 1.35 |
| N. of refl. | 9775 |
| Refl. with I > 2σ(I) | 4059 |
| R (I > 2σ(I)) | 4.71 |

Analysis was performed at room temperature using a Bruker Smart Apex diffractometer with graphite monochromated Mo Kα radiation equipped with a CCD detector. Data were collected using phi and omega scans (program used: SMART 5.6). No significant decay of standard intensities was observed. Data reduction (Lorentz and polarization corrections) and absorption correction were applied (program used: SAINT 5.0).

The structure was solved with direct methods and least-squares refinement of Fo2 against all measured intensities was carried out (program used: SHELXTL-NT 6.1). All non-hydrogen atoms were refined with anisotropic displacement parameters. The O atom of the water molecule lies in a two-fold axis.

The asymmetric unit of the crystal structure is depicted in FIG. 5, viewed nearly down the b axis (i.e., the twofold axis passing through the O of the water molecule is almost perpendicular to the plane of the drawing); intermolecular H bonds are indicated by dashed lines (only hydrogen atoms involved in H bonding have been included; program used: Mercury 2.4, C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Cryst., 41, 2008, 466-470).

(See FIG. 5—Single Crystal Structure).

Example 2

Preparation and Characterization of the Co-crystal Rosuvastatin Pyrazine Hydrate of Formula (IV)

(IV)

Preparation

To an assay tube equipped with magnetic stirrer containing Rosuvastatin (as acid form) (31 mg, 0.06 mmol) and pyrazine (250 mg, 3.1 mmol, 50 eq), water was added (0.3 mL) and the mixture was sonicated for 5 min before stirring for 3 h at room temperature. The resulting white suspension was centrifuged at room temperature (14000 rpm, 10 min), the supernatant liquid was discarded and the resulting solid was dried at vacuum to provide 17 mg of co-crystal Rosuvastatin pyrazine hydrate as a white solid for a molar yield of 50%.

1H-NMR Characterization

Proton nuclear magnetic resonance analyses were recorded in deuterated dimethyl sulfoxide (DMSO-d6) in a Varian Mercury 400 spectrometer, equipped with a broadband probe ATB 1H/19F/X of 5 mm. Spectra were acquired dissolving 5-10 mg of sample in 0.6 mL of deuterated solvent.

Figure 6:
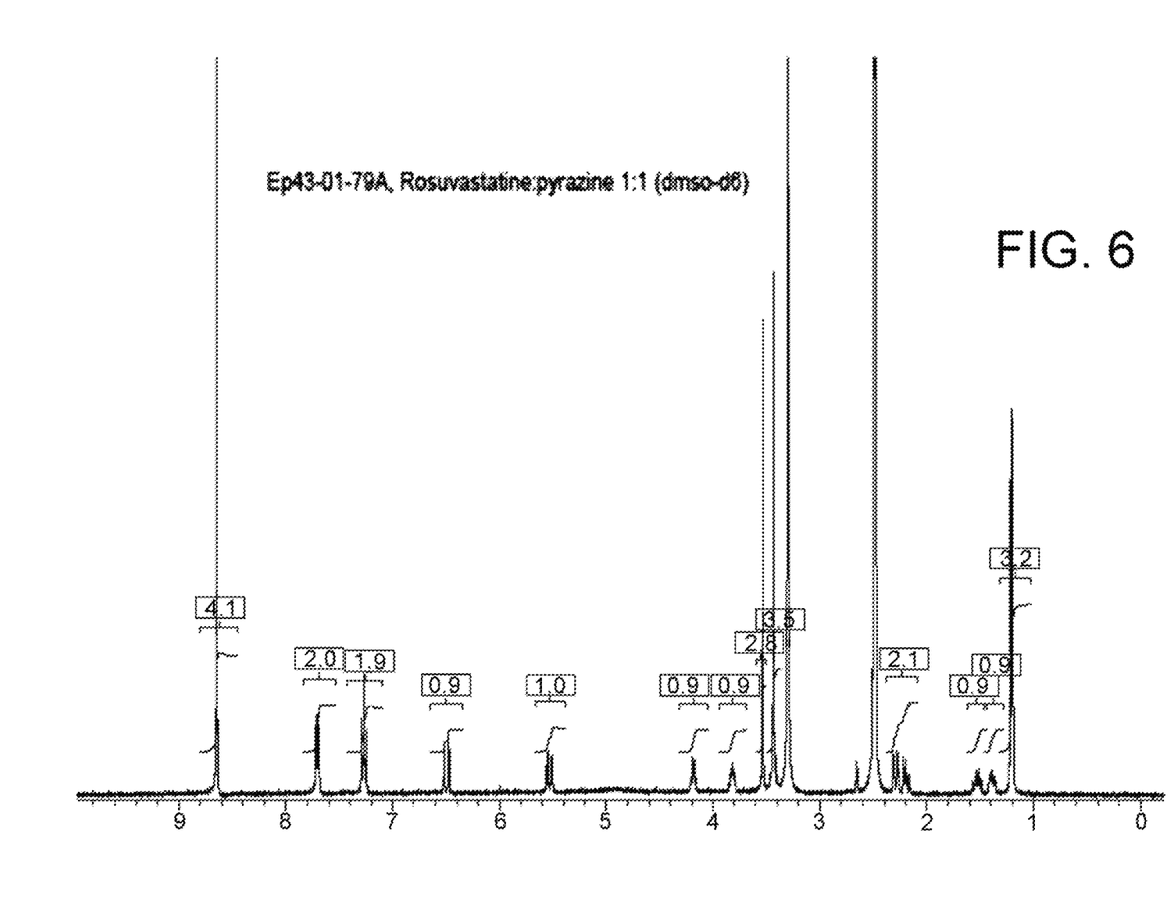
FIG. 6 shows a 1H-NMR spectrum of the co-crystal Rosuvastatin pyrazine hydrate of formula (IV).

1H-NMR (DMSO, 400 MHz): δ=8.66 (s, 4H); 7.77-7.67 (m, 2H); 7.33-7.23 (m, 2H); 6.51 (dd, J=1.2 Hz, J=16.0 Hz,

1H); 5.54 (dd, J=5.9 Hz, J=16.0 Hz, 1H); 4.20 (q, J=6.3 Hz, 1H); 3.89-3.78 (m, 1H); 3.55 (s, 3H); 3.50-3.39 (m, 4H); 2.31 (dd, J=4.7 Hz, J=14.8 Hz, 1H); 2.20 (dd, J=7.8 Hz, J=14.8 Hz, 1H); 1.60-1.49 (m, 1H); 1.45-1.34 (m, 1H); 1.22 (d, J=6.6 Hz, 6H). (See FIG. 6—1H-NMR)

Karl-Fischer Characterization

Karl Fischer analyses were recorded with a Metrohm 787 KF Trinito. Analyses of two samples of 28.1 mg and 36.8 mg were carried out using the following reactants: Hydranal-Composite 5 (Riedel de Haën Ref 34081), Hydranal Methanol Rapid (Riedel de Haën Ref 37817) and Hydranal Water Standard 10.0 (Riedel de Haën Ref 34849 used to calculate the factor).

The KF analysis of the co-crystal Rosuvastatin pyrazine hydrate shows 3.6% water (average of the two analyses) confirming that such co-crystal is a monohydrate form (calc. 3.1%).

X-Ray Powder Diffraction (XRPD) Characterization

XRPD analysis was performed using a Philips X'Pert diffractometer with Cu Kα radiation in Bragg-Brentano geometry. The system is equipped with a mono-dimensional, real time multiple strip detector. The diffractogram was recorded from 3° to 40° (2θ) at a scan rate of 17.6° per minute (See FIG. 7).

List of selected peaks (only peaks with relative intensity greater than or equal to 1% are indicated) in Table 5:

| Pos. [°2Th.] | d-spac. [Å] | Rel. Int. [%] |
|---|---|---|
| 9.36 | 9.45 | 100 |
| 9.69 | 9.13 | 11 |
| 11.77 | 7.52 | 11 |
| 12.52 | 7.07 | 7 |
| 14.11 | 6.28 | 76 |
| 14.76 | 6.00 | 7 |
| 15.33 | 5.78 | 24 |
| 16.30 | 5.44 | 3 |
| 18.04 | 4.92 | 12 |
| 18.74 | 4.73 | 10 |
| 19.05 | 4.66 | 21 |
| 19.80 | 4.48 | 12 |
| 21.03 | 4.22 | 16 |
| 21.52 | 4.13 | 53 |
| 21.82 | 4.07 | 21 |
| 22.10 | 4.02 | 46 |
| 23.57 | 3.78 | 13 |
| 24.30 | 3.66 | 4 |
| 24.64 | 3.61 | 5 |
| 25.16 | 3.54 | 7 |
| 25.80 | 3.45 | 15 |
| 28.07 | 3.18 | 5 |
| 28.45 | 3.14 | 5 |
| 29.31 | 3.05 | 4 |
| 30.26 | 2.95 | 3 |
| 30.93 | 2.89 | 5 |
| 31.26 | 2.86 | 2 |
| 32.95 | 2.72 | 1 |
| 34.33 | 2.61 | 4 |
| 35.84 | 2.51 | 2 |
| 36.57 | 2.46 | 2 |

Figure 7:
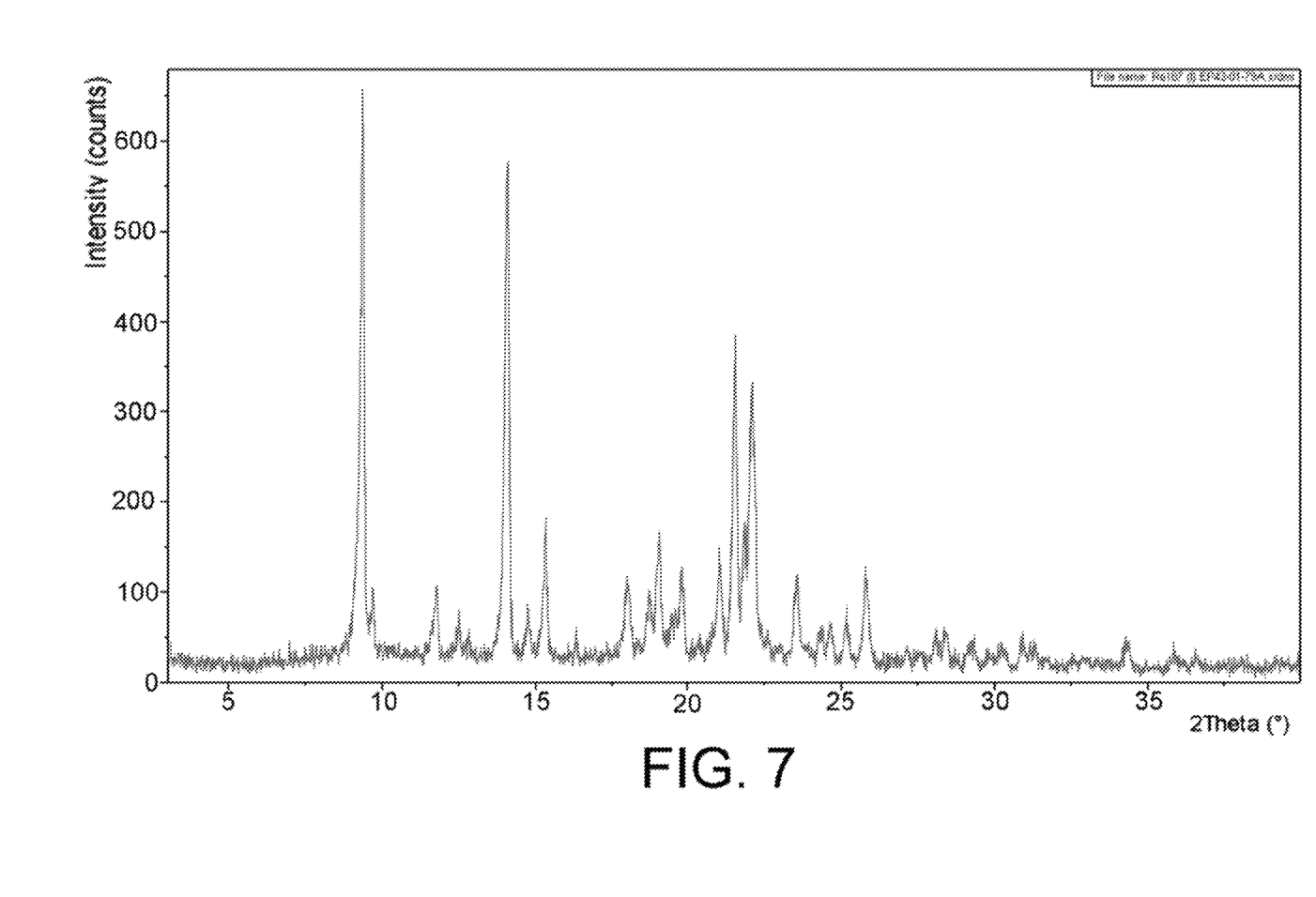
FIG. 7 shows a XPRD diffractogram of the co-crystal Rosuvastatin pyrazine hydrate of formula (IV).

(See FIG. 7—XRPD Diffractogram)

Example 3

Preparation and Characterization of the Co-crystal Rosuvastatin Quinoxaline (1:2) of Formula (V)

(V)

Preparation

To an assay tube equipped with magnetic stirrer containing 30 mg of Rosuvastatin (as acid form) (0.06 mmol) and 250 mg of quinoxaline (1.9 mmol, 30 eq) were added 0.3 mL of toluene and the crude was sonicated for 5 min before stirring for 20.5 h at room temperature. The resulting brown suspension was centrifuged at room temperature (14000 rpm, 10 min), the supernatant liquid was discarded and the resulting solid was dried under vacuum to provide 25.3 mg of the co-crystal Rosuvastatin quinoxaline (1:2) as a brown solid for a molar yield of about 55%.

1H-NMR Characterization

Proton nuclear magnetic resonance analyses were recorded in deuterated chloroform (CDCl3) in a Varian Mercury 400 spectrometer, equipped with a broadband probe ATB 1H/19F/X of 5 mm. Spectra were acquired dissolving 5-10 mg of sample in 0.6 mL of deuterated solvent.

Figure 8:
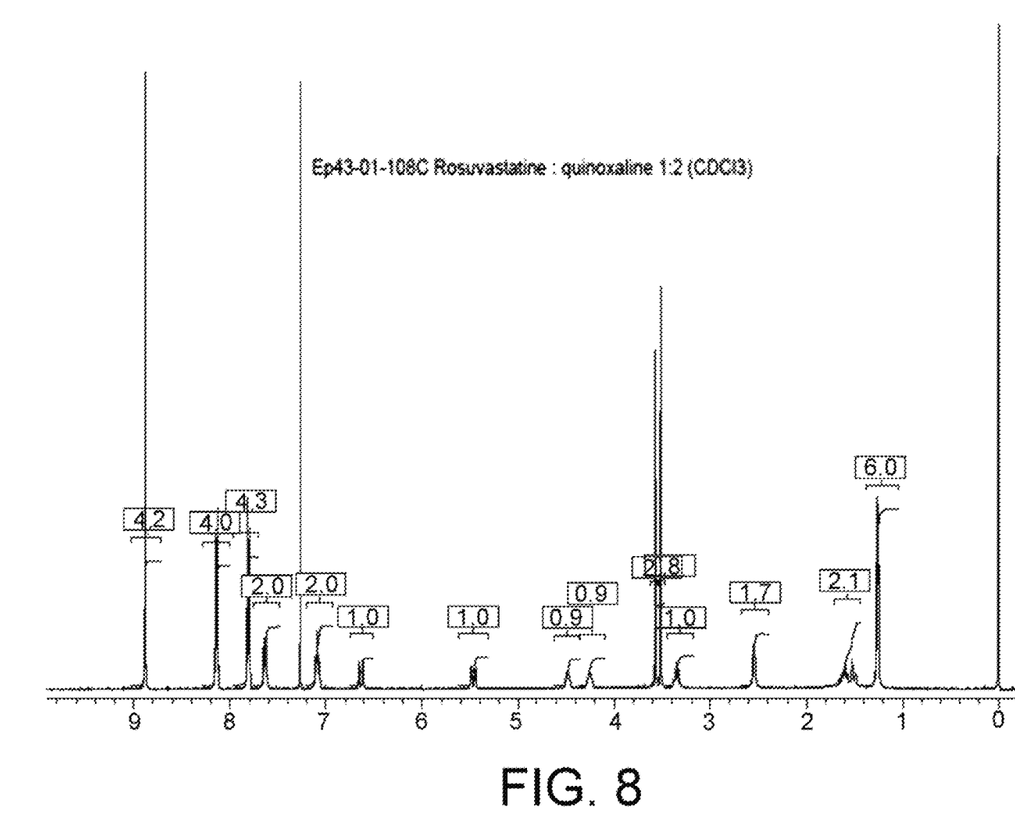
FIG. 8 shows a 1H-NMR spectrum of the co-crystal Rosuvastatin quinoxaline (1:2) of formula (V).

1H NMR (CDCl$_3$, 400 MHz): δ=8.90-8.86 (m, 4H); 8.18-8.09 (m, 4H); 7.86-7.76 (m, 4H); 7.68-7.59 (m, 2H); 7.13-7.04 (m, 2H); 6.63 (d, J=16.0 Hz, 1H); 5.47 (dd, J=5.5 Hz, J=16.0 Hz, 1H); 4.53-4.43 (m, 1H); 4.31-4.20 (m, 1H); 3.56 (s, 3H); 3.51 (s, 3H); 3.34 (q, J=6.6 Hz, 1H); 2.60-2.49 (m, 1H); 1.67-1.45 (m, 3H); 1.60-1.48 (m, 1H); 1.45-1.35 (m, 1H); 1.26 (d, J=6.6 Hz, 6H). (See FIG. 8—1H-NMR).

X-ray Powder Diffraction (XRPD) Characterization

XRPD analysis was performed using a Philips X'Pert diffractometer with Cu Kα radiation in Bragg-Brentano geometry. The system is equipped with a mono-dimensional, real time multiple strip detector. The diffractogram was recorded from 3° to 40° (2θ) at a scan rate of 17.6° per minute. (See FIG. 9)

List of selected peaks (only peaks with relative intensity greater than or equal to 1% are indicated) are shown in Table 6

| Pos. [°2Th.] | d-spac. [Å] | Rel. Int. [%] |
|---|---|---|
| 9.25 | 9.56 | 100 |
| 13.04 | 6.79 | 12 |
| 13.90 | 6.37 | 32 |
| 14.80 | 5.98 | 15 |
| 16.40 | 5.41 | 8 |
| 17.58 | 5.04 | 1 |
| 18.11 | 4.90 | 9 |
| 18.56 | 4.78 | 5 |
| 19.78 | 4.49 | 5 |
| 20.98 | 4.23 | 8 |
| 21.32 | 4.17 | 3 |
| 21.83 | 4.07 | 6 |
| 22.47 | 3.96 | 8 |
| 22.90 | 3.88 | 12 |
| 23.29 | 3.82 | 5 |
| 23.97 | 3.71 | 6 |
| 24.69 | 3.61 | 1 |
| 25.10 | 3.55 | 1 |
| 25.57 | 3.48 | 2 |
| 26.07 | 3.42 | 2 |
| 27.22 | 3.28 | 3 |
| 28.01 | 3.19 | 2 |
| 28.66 | 3.11 | 1 |
| 29.24 | 3.05 | 1 |
| 29.92 | 2.99 | 2 |
| 32.64 | 2.74 | 2 |
| 34.15 | 2.63 | 2 |

Figure 9:
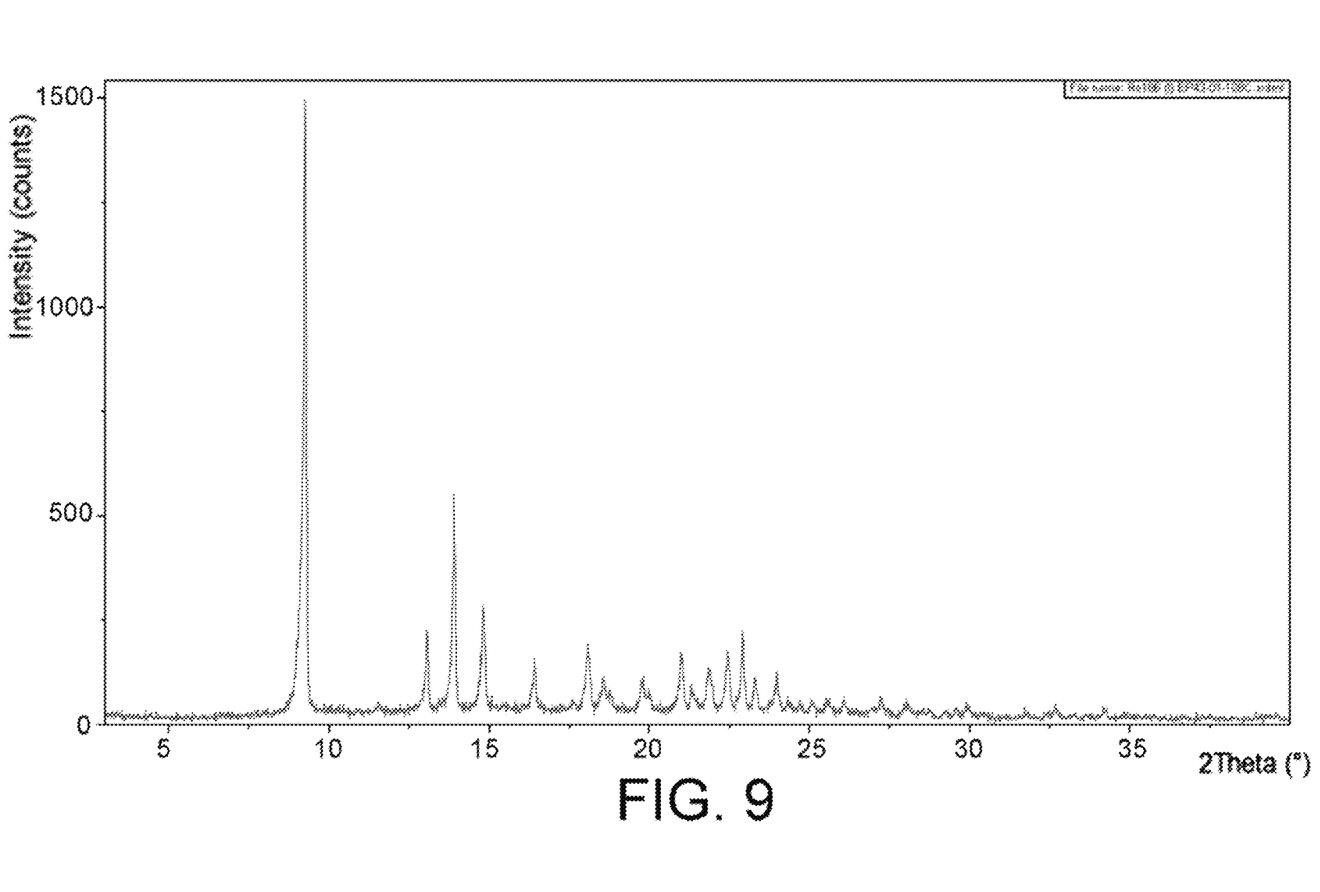
FIG. 9 shows a XPRD diffractogram of the co-crystal Rosuvastatin quinoxaline (1:2) of formula (V).

(See FIG. 9—XRPD Diffractogram.)

Example 4

Preparation of the Co-crystal Rosuvastatin 2-aminopyrimidine Hemihydrate of Formula (III) from a Solution Containing Rosuvastatin Sodium Salt (RSVNa)

To a 250 ml round bottomed flask equipped with magnetic stirrer and thermometer containing 60.0 g of an aqueous solution of RSVNa (250 g RSVNa in 1.5 kg of stock solution, 167 mg/g, 10 g of RSVNa, 20 mmol), methyl-isobutylketone (MIK) (23.3 ml, 2.1 vol.) was added before adding aqueous 3M HCl dropwise (13 ml, 39 mmol, 2 eq) at 0-5° C. After 5 min stirring at 0-5° C., the phases were separated and the aqueous layer was extracted with MIK (2×11.6 ml, 2×1 vol.). The combined organic phases were washed with water (11.6 ml, 1.2 vol). To the resulting organic phase, 2-aminopyrimidine (4.28 g, 45 mmol, 2.2 eq) were added. The mixture was gently warmed until a clear solution was obtained (30-35° C.). The solution was seeded with Rosuvastatin 2-aminopyrimidine hemihydrate and was allowed to cool to room temperature (if the solution is not seeded it might be necessary to wait longer to obtain the precipitation of the co-crystal). The yellow suspension was stirred for 5 h and was cooled to 0-5° C. for a further 1.5 h. The solid was filtered through a sintered glass funnel (n° 3) and washed with MIK saturated with water at 0-5° C. (2×11.5 ml, 2×1 vol.) and was dried under vacuum at room temperature to provide 8.20 g of co-crystal Rosuvastatin 2-aminopyrimidine hemihydrate as an off white solid for a molar yield of 70%.

Analysis of co-crystal Rosuvastatin 2-aminopyrimidine hemidrate:
XRPD: Crystalline form like the product of Example 1. (Traces of free 2-aminopyrimidine were observed.)
1H-NMR: A 1:1 ratio of Rosuvastatin:2-aminopyrimidine coformer was observed.
HPLC: The purity of the Rosuvastatin from the co-crystal is 99.96% (without taking account of the coformer 2-aminopyrimidine). The analysis of starting product RSVNa by HPLC in the same conditions shows a purity of 98.70%.

Example 5

Preparation of Rosuvastatin Calcium Salt (RSVCa) of Formula (II) from the Co-crystal Rosuvastatin 2-Aminopyrimidine Hemihydrate of Formula (III)

To a 25 ml round bottomed flask equipped with magnetic stirrer containing a crude co-crystal Rosuvastatin 2-aminopyrimidine hemihydrate (1.0 g) (containing, by NMR estimation, 860 mg of co-crystal (1.47 mmol) and 140 mg of 2-aminopyrimidine), was added aqueous 2M NaOH (2 ml, 4 mmol, 2.7 eq.). A yellow solution was obtained and water (8 mL) was added. The aqueous solution was washed with MIK (2×3 mL) and the aqueous phase was partially concentrated on a rotatory evaporator to remove traces of MIK (1.7 g of solvent was distilled). To the resulting solution, aqueous 1.8 M CaCl2·2H2O (1 mL, 1.8 mmol, 1.22 eq.) was added dropwise during 10 min, to provide a yellowish suspension. The mixture was filtered through a sintered glass funnel (n° 4), washed with water (2×3 mL) and dried under vacuum at 40° C. (5 h) to provide 581 mg of Rosuvastatin Calcium (RSVCa) as an off-white solid with a molar yield of 79%. HPLC purity: 99.64% (and 0.28% of residual 2-aminopirimidine coformer).

Example 6

Preparation of Rosuvastatin Calcium Salt (RSVCa) of Formula (II) Free from the Residual Coformer 2-aminopyrimidine To a 10 mL round bottomed flask equipped with magnetic stirrer containing the previous sample of Rosuvastatin Calcium of Example 5 (248 mg, 0.5 mmol), water was added (2.5 mL, 10 vol.). The mixture was stirred at 50° C. for 1 h and then allowed to cool to room temperature before stirring for a further 80 min. The mixture was filtered through a sintered glass funnel (n° 4), washed twice with water (2×0.5 mL, 2×2 vol.) and dried under vacuum at room temperature to provide 204 mg of Rosuvastatin Calcium (RSVCa) as an off-white solid with a molar yield of 82%. This product has a HPLC purity of 99.94%. Karl Fischer analysis indicates a 5.7% water content after drying for 6 h at room temperature under vacuum (4-8 mbar).

The analysis by XRPD shows amorphous RSVCa.

Example 7

Preparation of the Co-crystal Rosuvastatin 2-aminopyrimidine Hemihydrate of Formula (III) from a Solution Containing Rosuvastatin Sodium Salt (RSVNa)

To a 250 ml round bottomed flask equipped with magnetic stirrer and thermometer containing 60.0 g of an aqueous solution of RSVNa (230 g RSVNa in 1.5 kg of stock solution, 153 mg/g, 9.2 g of RSVNa, 18.4 mmol), was added methyl-isobutylketone (MIK) (23.3 ml, 2.1 vol.) before adding aqueous 3 M HCl dropwise (13 ml, 39 mmol, 2.1 eq) at 0-5° C. until reaching a pH of 1.7. After 5 min stirring at 0-5° C., the phases were separated and the aqueous layer was extracted with MIK (2×11.6 ml, 2×1 vol.). The combined organic phases were washed with water (11.6 ml, 1.2 vol). To the resulting organic phase, 2-aminopyrimidine (4.28 g, 45 mmol, 2.45 eq) was added. The mixture was gently warmed until a clear solution was obtained (30-35° C.). The solution was seeded with co-crystal Rosuvastatin 2-aminopyrimidine hemihydrate and was allowed to cool to room temperature. The yellow suspension was stirred for 5 h and was cooled to 0-5° C. for a further 1.5 h. The solid was filtered through a sintered glass funnel (n° 3) and was washed with MIK saturated with water at 0-5° C. (2×11.5 ml, 2×1 vol.) and was dried under vacuum at room temperature to provide 8.20 g of co-crystal Rosuvastatin 2-aminopyrimidine hemihydrate as an off white solid with a molar yield of 77%.

Example 8

Preparation of Rosuvastatin Calcium Salt (RSVCa) of Formula (II) Free from the Residual Coformer 2-aminopyrimidine To a 10 mL round bottomed flask (equipped with magnetic stirrer) containing Rosuvastatin calcium (248 mg, 0.5 mmol), water was added (2.5 mL, 10 vol.). The mixture was stirred at 50° C. for 1 h and then allowed to cool to room temperature before stirring for a further 80 min. The mixture was filtered through a sintered glass funnel (n° 4), washed twice with water (2×0.5 mL, 2×2 vol.) and dried under vacuum at room temperature to provide 204 mg of RSVCa as an off-white solid with a molar yield of 82%.

This product has a purity by HPLC of 99.94% with only trace amounts of 2-aminopyrimidine. Karl Fischer analysis indicates a 5.7% water content after drying for 6 h at room temperature under vacuum (4-8 mbar).

In particular, it could be appreciated how the use of the co-crystals of Rosuvastatin object of the present invention as synthetic intermediates allows the preparation of Rosuvastatin Calcium in a form extremely pure and with high molar yields.

Example 9

Single Crystal Structure of Co-crystal Rosuvastatin 2-aminopyrimidine Hemihydrate The single crystal confirmed the formation of a co-crystal.
Asymmetric Unit of the Co-crystal
View of the asymmetric unit of the crystal structure viewed nearly along the b axis (the twofold axis passes through the oxygen of the water molecule). Only hydrogen atoms involved in H bonding have been included. Intermolecular hydrogen bonds are shown (program used: Mercury 2.4, C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Cryst., 2008, 41, 466-470). (See FIG. 5—Single crystal structure.)
Structural Analysis
From crystal structure determination by single crystal X ray diffraction it can be inferred that the co-crystal Rosuvastatin 2-aminopyrimidine hemihydrate crystalline phase is a co-crystal, not a salt, as both molecules are non-ionized.

The difference electronic density maps from the structural refinement indicate the presence of one hydrogen atom bonded to one of the oxygen atoms of the carboxy group (thus being a carboxylic group) of the Rosuvastatin molecule. If a salt were formed, no H atoms would be bound to any of the O atoms of the carboxy group, thus being a carboxylate group.

The electronic density maps from the refinement of the structure indicate the presence of two hydrogen atoms bonded to the nitrogen atom of the primary amino group of the 2-aminopyrimidine molecule. If a salt were formed, three H atoms would be bound to this N atom.

The two C—O distances of the carboxy group of the Rosuvastatin molecule are 1.215 Å and 1.295 Å. These values are in good agreement with a C═O (carbonyl) group and a C—OH (alcohol) group, respectively. If a salt were formed, the two distances of the carboxylate would be more similar, close to an intermediate value between the two aforementioned distances.

In the 2-aminopyrimidine molecule, the primary amino N and the three atoms bound to it (two H and the C of the ring) lie approximately in the same plane. If a salt were formed, there would be a third H atom bound to this N which would result in a tetrahedral bond arrangement around it.

Example 10

Rule of Co-crystal Prediction Using pKa Values

The formation of a salt or a co-crystal can be predicted from the pKa values of the components of the crystal form (acid (AH) and base (B)). The transfer of a proton can be determined by the following equation:

$$\Delta pKa = pKa(\text{conjugate acid of the base } B) - pKa (\text{acid } AH)$$

It is generally accepted that for ΔpKa greater than 3, salts of the type B+–H•••A– are formed. If ΔpKa is less than 0, a cocrystal B•••AH will be almost exclusively obtained. In the ΔpKa range of 0 to 3, the prediction is poor and even complexes with partial proton transfer can be observed. (1), (2).

The pKa of pyrazine and quinoxaline are respectively 0.6 and 0.56 whereas the pKa of rosuvastatin (RSV) is 4.6. So, in both cases there is a ΔpKa of –4, a negative value far enough from 0 to assume the formation of a co-crystal. Crystal forms of Rosuvastatin pyrazine hydrate, Rosuvastatin quinoxaline (1:2) according to the equation are thus co-crystals.

Literature References (1) Johnson, S. L., Rumon, K. A. Infrared spectra of solid 1:1 pyridine-benzoic acid complexes; the nature of the hydrogen bond as a function of the acid base levels in the complex. J. Phys. Chem., 1965, 69, 74-86

(2) Childs, S. L., Stahly, G. P., Park, A. The Salt-Cocrystal Continuum: The Influence of Crystal Structure on Ionization State, Mol. Pharm., 2007, 4(3), 323-338.

Example 11

Stability Studies at 40° C. Under Vacuum of Co-crystal Rosuvastatin 2-Aminopyrimidine Hemihydrates Compared to Rosuvastatin The starting products Rosuvastatin (in acid form) (RSV) and co-crystal Rosuvastatin 2-aminopyrimidine hemihydrate of these stability studies have a lactone impurity content of 17.267% and 0.036% respectively. The co-crystal has only 3 impurities at 5.651, 5.948 and 6.674 (lactone) min.

For RSV, only some impurities (impurities in common with the co-crystal or impurities with a significant variation) were studied.

Storage conditions: 40° C. under vacuum for 20 and 40 hours.

Result: for the co-crystal, the increases of the impurities 5.651 and 5.948 min were negligible while the lactone content increased a little (0.036% to 0.091%). No new impurities were observed.

In the case of RSV, the lactone content increased significantly with time (17.27 to 39.84%), but between 20 h and 40 h the rate of formation seems to decrease. Other impurities in RSV increased with time.

In conclusion, the stability of co-crystal is higher than the stability of the Rosuvastatin acid (RSV). At 40° C. after 40 h only a slight increase of lactone was observed, while for the RSV the amount of lactone and other impurities increased strongly (especially for the lactone impurity).

The invention claimed is:

1. A method for preparing Rosuvastatin or its salts comprising:
   (a) preparing a co-crystal of Rosuvastatin selected from the group consisting of:
      1. Rosuvastatin 2-aminopyrimidine hemihydrate,
      2. Rosuvastatin pyrazine hydrate, and
      3. Rosuvastatin quinoxaline (1:2); and
   (b) converting the co-crystal prepared in step (a) to the Rosuvastatin of formula (I)

(I)

or a salt thereof.

2. The method of claim 1, wherein Rosuvastatin is a calcium salt.

3. The method of claim 1 wherein step (a) further comprises the addition of a coformer to a solution of Rosuvastatin in toluene, MIK or water.

4. The method of claim 1 wherein step (a) is performed at a temperature below about 40° C.

5. A co-crystal of Rosuvastatin selected from the group consisting of:
   Rosuvastatin 2-aminopyrimidine hemihydrate,
   Rosuvastatin pyrazine hydrate, and
   Rosuvastatin quinoxaline (1:2).

6. The co-crystal of Rosuvastatin of claim 5 consisting of Rosuvastatin 2-aminopyrimidine hemihydrate.

7. The co-crystal of Rosuvastatin of claim 6 having an X-Ray Powder Diffractogram (XRPD) with characteristic peaks expressed in 2 Theta value of: 9.40 (vs), 13.50 (s), 14.08 (m), 15.15 (m), 18.59 (m), 21.67 (m), 22.16 (m), 22.21 (m), 22.66 (m), (+/−) 0.10; wherein (vs)=very strong intensity, (s)=strong intensity, and (m)=medium intensity.

8. The co-crystal of Rosuvastatin of claim 6 having a melting point of about 109.4° C.

9. A method for treating conditions associated with hypercholesterolemia comprising administering a co-crystal of Rosuvastatin according to claim 5.

10. The method of claim 9 wherein the co-crystal of Rosuvastatin is the co-crystal Rosuvastatin pyrazine hydrate.

11. A pharmaceutical composition comprising the co-crystal of Rosuvastatin according to claim 5 and one or more pharmaceutically acceptable excipients, carriers and/or diluents.

12. A process for the preparation of a co-crystal of Rosuvastatin of claim 5 comprising the addition of a coformer selected from the group consisting of:
   2-aminopyrimidine,
   pyrazine, and
   quinoxaline;
to a solution comprising Rosuvastatin.

* * * * *